United States Patent

Sato et al.

[11] Patent Number: 4,966,969
[45] Date of Patent: Oct. 30, 1990

[54] PROCESS FOR THE PREPARATION OF TRIETHYLENEDIAMINES

[75] Inventors: Haruhito Sato; Masanori Tsuzuki, both of Sodegaura, Japan

[73] Assignee: Idemitsu Kosan Company Limited, Tokyo, Japan

[21] Appl. No.: 481,661

[22] Filed: Feb. 14, 1990

Related U.S. Application Data

[63] Continuation of Ser. No. 116,009, Oct. 30, 1987, abandoned.

[30] Foreign Application Priority Data

Nov. 10, 1986 [JP] Japan .................................. 61-267228

[51] Int. Cl.$^5$ ..................... C07D 487/08; B01J 29/28; B01J 23/08; B01J 21/02
[52] U.S. Cl. ...................................... 544/352; 544/351
[58] Field of Search ............................... 544/351, 352

[56] References Cited

FOREIGN PATENT DOCUMENTS 158319 10/1985 European Pat. Off. .

*Primary Examiner*—Mark L. Berch
*Attorney, Agent, or Firm*—Frishauf, Holtz, Goodman & Woodward

[57] ABSTRACT

The present invention relates to a process for preparing triethylenediamines which comprises contacting an amine compound having, in the molecule, a group represented by the general formula:

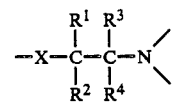

(wherein $R^1$, $R^2$, $R^3$ and $R^4$ are independently a hydrogen atom or an alkyl group having 1 to 4 carbon atoms and X is nitrogen or oxygen) with a catalyst comprising crystalline metallosilicate having a silica ($SiO_2$)/metal oxide ($M_2O_3$) molar ratio of 12/1 or more under a pressure of not less than 4 kg/cm$^2$(absolute pressure).

According to the present invention, the conversion of the amine compound can be greatly increased and thus the desired triethylenediamines can be produced in a high yield.

6 Claims, No Drawings

PROCESS FOR THE PREPARATION OF TRIETHYLENEDIAMINES

This application is a continuation of application Ser. No. 07/116,009, filed Oct. 30, 1987 now abandoned.

BACKGROUND OF THE INVENTION

The present invention relates to a process for the preparation of triethylenediamines and more particularly to a process for efficiently preparing triethylenediamines from amine compounds having, in the molecule, a group represented by the general formula:

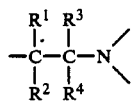

(wherein $R^1$, $R^2$, $R^3$ and $R^4$ are independently a hydrogen atom or an alkyl group having 1 to 4 carton atoms) by the use of specified crystalline metallosilicate as a catalyst under a pressure of at least 3 kilograms per square centimeter (kg/cm$^2$) (absolute pressure).

A process for preparing triethylenediamines by contacting certain amino compounds with high silica zeolite having a SiO$_2$/Al$_2$O$_3$ molar ratio of 20/1 or more, at a reaction temperature of 250° to 550° C., a space velocity of 200 to 2,500 hr$^{-1}$ and a reaction pressure of 0.5 to 2 kg/cm$^2$ (absolute pressure) has been developed and is disclosed in Japanese Patent Application Laid-Open No. 260574/1985.

The above process, however, is unsuitable for practical use because the conversion of the amino compound starting material is low.

SUMMARY OF THE INVENTION

The present invention is intended to overcome the above prior art problems, and an object of the present invention is to provide a method whereby triethylenediamines can be prepared in high yields.

It has been found that the above object is attained by using amine compounds having, in the molecule, a group represented by the general formula:

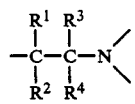

(wherein $R^1$, $R^2$, $R^3$ and $R^4$ are independently a hydrogen atom or an alkyl group having 1 to 4 carbon atoms) as the starting material and specified crystalline metallosilicate as a catalyst, and by reacting the starting material under a pressure of at least 3 kg/cm$^2$ (absolute pressure), preferably at least 4 kg/cm$^2$ (absolute pressure).

The present invention relates to a process for preparing triethylenediamines by contacting amine compounds having, in the molecule, a group represented by the general formula:

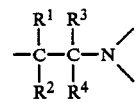

(wherein $R^1$, $R^2$, $R^3$ and $R^4$ are the same as defined above) with a crystalline metallosilicate-containing catalyst in which the molar ratio of silica (SiO$_2$) to metal oxide (M$_2$O$_3$), i.e., SiO$_2$/M$_2$O$_3$, is at least 12/1, under a pressure of at least 3 kg/cm$^2$ (absolute pressure).

DETAILED DESCRIPTION OF THE INVENTION

Triethylenediamines to be prepared in the present invention are compounds represented by the general formula:

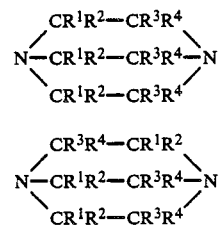

(wherein $R^1$, $R^2$, $R^3$ and $R^4$ are the same as defined above).

As the starting material to be used in the process of the present invention, any amine compounds having, in the molecule, a group represented by the general formula:
(wherein $R^1$, $R^2$, $R^3$ and $R^4$ are the same as defined above) can be used. Typical examples of the amine compounds are monoethanolamine, isopropanolamine, N-hydroxyethylpiperazine, N-aminoethylpiperazine, diethanolamine, diisopropanolamine, triethanolamine, piperazine, morpholine, ethylenediamine, diethylenetriamine and triethylenetetramine all include the group having the formula

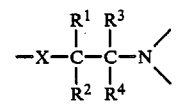

wherein X is oxygen or nitrogen.

The crystalline metallosilicate which is used as the catalyst in the process of the present invention has a crystal skeleton mainly comprised of silicon dioxide (SiO$_2$) and metal oxide (M$_2$O$_3$ (wherein M represents a metal)). The molar ratio of SiO$_2$ to M$_2$O$_3$ (SiO$_2$/M$_2$O$_3$) is 12:1 or more and preferably 40:1 to 3,000:1 and more preferably 40:1 to 1,000:1. If the SiO$_2$ to M$_2$O$_3$ molar ratio is less than 12:1, the yield of triethylenediamines is undesirably low.

There are no special limitations to the crystalline metallosilicate as used herein as long as it satisfies the above SiO$_2$ to M$_2$O$_3$ molar ratio. Crystalline metallosilicates having a main pore made of ten-membered ring of oxygen, especially those belonging to members of the pentasil type structure are preferred. The metal (M) constituting the crystalline metallosilicate is preferably a trivalent metal. Representative examples are aluminum (Al), gallium (Ga), boron (B), iron (Fe), indium (In), lanthanum (La), scandium (Sc), yttrium (Y), chromium (Cr) and titanium (Ti). One or more of these metals are used.

Representative examples of the crystalline metallosilicates as described above include ZSM-5 described in U.S. Pat. No. 3,790,471, etc., ZSM-8 described in Japanese Patent Application Laid-Open No. 25097/1972, and ZSM-11 described in Japanese Patent Publication No. 23280/1978. In addition, crystalline aluminosilicates such as ZSM-35 described in Japanese Patent Application Laid-Open No. 139029/1977 and ZSM-21 described in U.S. Pat. No. 4,001,346, etc. can be used provided that $SiO_2/M_2O_3$ is 12 or larger.

The crystalline metallosilicate wherein M is B includes crystalline borosilicate having the ZSM-5 type structure or the ZSM-11 type structure as described in Japanese Patent Application Laid-Open Nos. 55500/1978 and 7598/1980.

The crystalline metallosilicate wherein M is Fe includes crystalline ferrosilicate, such as ferrierite, as described in *Journal of Catalysis*, Vol. 35, pages 256–272 (1974), Japanese Patent Application Laid-Open Nos. 127898/1975 and 85415/1980.

The crystalline metallosilicate wherein M is Ga includes crystalline gallosilicate having the ZSM-5 type structure, such as gallosilicate, as described in Reference Example 3 as described hereinafter.

The crystalline metallosilicate wherein M is In, La, Sc, Y, Cr, Ti, Be or Mn includes a crystalline metallosilicate having the structure that the Al cation incorporated in the skeleton of the aforementioned crystalline aluminosilicate is replaced by the cation of In, La, Sc, Y, Cr, Ti, Be or Mn, respectively.

Crystalline metallosilicates of pentasil family, such as ZSM-5, as obtained by the hydrothermal synthesis using an organic crystallizing agent are preferred.

The crystalline metallosilicate which is used in the present invention can be prepared by known methods.

For example, a pentasil type crystalline metallosilicate which is an example of the aforementioned ZSM-5 type zeolite can be prepared by the hydrothermal synthesis using a mixture composed mainly of a silica source, e.g., colloidal silica, silica gel, or silicic acid salts such as water glass, and a metal oxide ($M_2O_3$) source, e.g., the sulfuric acid salts, nitric acid salts or oxyacid salts of the metal element M, such as aluminum sulfate, gallium nitrate, boric acid, ferric sulfate, chromium sulfate and sodium aluminate, in the presence or in the absence of an organic crystallizing agent, e.g., amines such as tetraalkylammonium halide having 2 to 5 carbon atoms.

There is also known a method in which the hydrothermal synthesis is performed in the presence of alkali metal compounds such as the hydroxides and halides of alkali metals such as sodium and the like.

The crystalline metallosilicate obtained by these methods is generally not of the $H^+$ type but of the type that $H^+$ is replaced by quaternary ammonium ion and/or alkali metal ion such as $Na^+$ and the like. It is preferred, therefore, that the crystalline metallosilicate be changed into the $H^+$ type. This exchange can be easily achieved by known methods.

For example, the quaternary ammonium ion can be changed into $H^+$ by calcining in the air at a temperature of about 500° to 600° C. For changing alkali metal ion such as $Na^{30}$ into $H^+$, there is often employed a method in which an alkali metal salt type crystalline metallosilicate is treated with an aqueous solution of ammonium salts such as ammonium nitrate and ammonium chloride to form an ammonium salt type crystalline metallosilicate and then the ammonium salt type crystalline metal silicate is calcined in the air at a temperature of 300° to 600° C. to obtain a $H^+$ type crystalline metallosilicate.

In addition, a method in which the alkali metal salt of crystalline metallosilicate is treated directly with a diluted acid such as diluted hydrochloric acid can be employed.

As well as the methods as described above, various methods can be employed for the preparation of the crystalline metallosilicate as used herein.

It is to be noted, however, that the present invention is not limited to the catalysts which have been prepared by the specified preparation methods.

The crystalline metallosilicate as used herein is preferably of the $H^+$ type. In the crystalline metallosilicate as used herein, $H^+$ may be partially or entirely replaced by other cations such as magnesium ion, calcium ion and lanthanum ion as long as the object of the present invention can be attained. Moreover, the aluminum atom constituting the crystal skeleton may be partially replaced by other metals such as Ga, B, Fe, In, La, Sc, Y, Cr and Ti.

The catalyst of the present invention can be used in any desired form such as in the form of powder, particles, strips, sphere and pellets. In order to mold the catalyst in a desired form, it is preferred that a binder such as silica, alumina, or silica-alumina be mixed with the above crystalline metallosilicate.

In the hydrothermal synthesis of the crystalline metallosilicate by compounding an organic compound such as quaternary amines according to the present invention, in order to increase catalytic activity, it is preferred to calcine the above crystalline metallosilicate in a stream of air and/or inert gas such as nitrogen prior to the reaction.

The conditions of calcination vary with the type of the crystalline metallosilicate, the extent to which quaternary ammonium ion and structure water remain, etc. Usually, organic compounds in the metallosilicate are removed by heating at a temperature of 400° to 600° C., preferably 450° to 550° C. for a time of more than 1 hours, preferably more than 3 hours.

In accordance with the process of the present invention, the desired triethylenediamines can be efficiently obtained by reacting the amine compounds having, in the molecule, a group represented by the general formula:

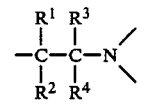

(wherein $R^1$, $R^2$, $R^3$ and $R^4$ are the same as defined above) as the starting material by the use as a catalyst of the crystalline metallosilicate and under a pressure of at least 3 kg/cm² (absolute pressure), preferably at least 4 kg/cm² (absolute pressure) and most preferably 6 to 150 kg/cm² (absolute pressure). If the reaction pressure is less than 3 kg/cm², the conversion of the amine compound as the starting material is undesirably very low.

The reaction of the amine compound proceeds on contacting it with a catalyst comprising the aforementioned crystalline metallosilicate under the above specified pressure. In this case, reaction conditions such as reaction temperature, reaction time and starting material/catalyst ratio cannot be determined unconditionally because they vary with the type of the amine compound, the type of the crystalline metallosilicate, reaction pressure, etc. Usually the reaction temperature is chosen within the range of 200° to 550° C., preferably 250° to 450° C.

The reaction is performed batchwise or continuously. In the case of the batchwise reaction, the reaction time should be 10 minutes to 48 hours, with the range of 1 to 10 hours being preferred. In the case of the continuous reaction, GHSV (weight hourly space velocity) is not critical, but usually 100 to 20,000 hr$^{-1}$. The preferred GHSV is determined depending on the temperature. For example, it 200 to 2,000 hr$^{-1}$ at the reaction temperature of 300° C., and at the reaction temperature of 350° C., 1,000 to 10,000 hr$^{-1}$.

In the reaction of the amine compound as the starting material according to the process of the present invention, the amine compound may be diluted with an inert gas such as hydrogen gas, nitrogen gas, steam or hydrocarbons, or with an inert solvent such as water and inert hydrocarbons. By using these diluents, the reaction can be controlled appropriately.

In the case of the batchwise reaction, it is also effective to proceed the reaction while distillying away the triethylenediamines as the reaction product.

The amount of the crystalline metallosilicate to be used as the catalyst in the process of the present invention varies with the type of the catalyst, the type of the amine compound as the starting material, and so on. In the case of the batchwise reaction, the amount of the crystalline metallosilicate used is sufficient to be 0.1 to 100% by weight, preferably 1 to 10% by weight based on the weight of the amine starting material.

After the reaction is completed, the catalyst is removed by a solid-liquid separation operation. The triethylenediamines may be isolated and purified by distillation, for example. In the case of the batchwise reaction, the triethylenediamines may be taken out of the reaction system by distillation without separation or removal of the catalyst. The unreacted amine compound recovered by the distillation operation can be again used as the starting material.

The crystalline metallosilicate to be used as the catalyst in the process of the present invention can be used repeatedly as a high activity catalyst by appropriately applying a calcining operation for reproduction.

The present invention produces various advantages. Some of the advantages are shown below.

Various amine compounds can be used as the starting material.

By increasing the reaction pressure up to at least 3 kg/cm$^2$ (absolute pressure), the conversion of the amine starting material can be greatly increased and thus the desired triethylenediamines can be produced in a high yield.

The selectivity of the triethylenediamines can be greatly increased by choosing a suitable GHSV.

Since the crystalline metallosilicate used in the present invention is excellent in thermal stability, it can be used at relatively high temperatures. Therefore the rate of reaction can be maintained at sufficiently high levels, and the catalytic activity can be maintained at high levels for long periods of time. Furthermore the catalyst can be used repeatedly by applying reproduction treatment. Accordingly the process of the present invention is low in production costs in comparison with the conventional methods and is greatly useful from an industrial standpoint.

The triethylenediamines produced by the process of the present invention can be utilized as the curing agent for polyurethane and epoxy resins.

The present invention is described in greater detail with reference to the following examples.

REFERENCE EXAMPLE 1

Preparation of Crystalline Aluminosilicate (I)

In 250 milliliters (ml) of water was dissolved 7.5 grams (g) of aluminum sulfate, and then 17.6 g of concentrated sulfuric acid and 26.3 g of tetra-n-propylammonium bromide were dissolved therein to form Solution A. Separately, 211.0 g of water glass (J sodium silicate No. 3, produced by Nippon Kagaku Kogyo Co., Ltd.) was dissolved in 250 ml of water to form Solution B. Separately, 79.0 g of sodium chloride was dissolved in 122 ml of water to form Solution C.

Solutions A and B were dropped at the same time to Solution C at room temperature over 10 minutes. The resultant mixture was placed in an autoclave and heated at 170 degrees centigrade (°C.) for 20 hours. The reaction mixture was cooled, and the contents were filtered off, washed with water and then dried at 120° C., for 12 hours. An X-ray diffraction analysis showed that the product was ZSM-5.

On calcining the ZSM-5 thus obtained, at 550° C for 6 hours, 56.5 g of sodium type ZSM-5 was obtained. This sodium type ZSM-5 was added to a 5-fold weight of a 1N aqueous ammonium nitrate solution, which was then refluxed for 8 hours. Then the reaction mixture was cooled and allowed to stand. The supernatant was removed by decantation. Thereafter, the reflux-decantation operation was repeated three times. The contents were filtered off, washed with water and then dried at 120° C for 12 hours to obtain ammonium type ZSM-5. In this ammonium type ZSM-5, SiO$_2$/Al$_2$O$_3$ (molar ratio) =90/1.

On calcining the ammonium type ZSM-5 in the air at 550° C. for 4 hours, H type ZSM-5, i.e., crystalline aluminosilicate (I) was obtained.

REFERENCE EXAMPLE 2

Preparation of Crystalline Aluminosilicate (II)

Crystalline aluminosilicate (II) was prepared in the same manner as in Reference Example 1 except that the amount of aluminum sulfate used was changed to 15.0 g.

In this crystalline aluminosilicate (II), SiO$_2$/Al$_2$O$_3$ (molar ratio) =45/1.

REFERENCE EXAMPLE 3

Preparation of Crystalline Aluminosilicate (III)

Crystalline aluminosilicate (III) was prepared in the same manner as in Reference Example 1 except that the amount of aluminum sulfate used was changed to 1.7 g.

In this crystalline aluminosilicate (III), SiO$_2$/Al$_2$O$_3$ (molar ratio) =400/1.

REFERENCE EXAMPLE 4

Preparation of Crystalline Gallosilicate

In 62 ml of water were dissolved 2.34 of gallium nitrate, 4.42 g of concentrated sulfuric acid and 6.58 g of tetra-n-propylammonium bromide to form Solution A. Separately, 52.78 g of water glass (J sodium silicate No. 3, produced by Nippon Kagaku Kogyo Co., Ltd.) was dissolved in 62 ml of water to form Solution B. Separately, 19.75 g of sodium chloride wa dissolved in 30 ml of water to form Solution C.

Solutions A and B were dropped at the same time to Solution C. The resultant mixture was placed in an autoclave and reacted at a reaction temperature of 170° C. for 24 hours. After cooling, the contents of the autoclave were filtered off, washed with water, dried at 120° C. for 12 hours and then calcined at 600° C. for 6 hours to obtain 9.6 g of sodium type crystalline gallosilicate.

The crystalline gallosilicate thus obtained was added to a 5-fold weight of a 1N ammonium nitrate solution, which was then heated at 80° C. for 8 hours, cooled and then filtered. Thereafter, the operation of heating and filtration of the solids was repeated three times. The solids were washed with water and dried at 120° C. for 16 hours to obtain ammonium type crystalline gallosilicate.

In this crystalline gallosilicate, $SiO_2/Ga_2O_3$ (molar ratio) =75.5/1. An X-ray diffraction analysis showed that the crystalline gallosilicate had the ZSM-5 structure.

On calcining the ammonium type crystalline gallosilicate in the air at 550° C. for 4 hours, H type crystalline gallosilicate was obtained.

REFERENCE EXAMPLE 5

Preparation of Crystalline Borosilicate

In 325 ml of water was dissolved 2.54 g of boron oxide, and 73.32 g of concentrated sulfuric acid and 88.08 g tetra-n-propylammonium bromide were added thereto to form Solution A. Separately, 686.14 g of water glass (trade name "J Sodium Silicate No. 3", produced by Nippon Kagaku Kogyo Co., Ltd.) was dissolved in 325 ml of water to form Solution B. Separately, 125.65 g of sodium chloride was dissolved in 182 ml of water to form Solution C.

Solutions A and B were dropped at the same time to Solution C. The resultant mixture was placed in an autoclave and heated at 170° C. for 20 hours. After cooling, the contents were filtered off, washed with water, dried at 120° C. for 12 hours and then calcined at 550° C. for 6 hours to obtain 140.3 g of sodium type crystalline borosilicate.

The crystalline borosilicate thus obtained was added to a 5-fold weight of a 1N aqueous ammonium nitrate solution, which was then refluxed for 8 hours. After cooling, the supernatnat was removed by decantation. Thereafter the operation of reflux and decantation was repeated three times. The contents were filtered off, washed with water, and dried at 120° C. for 12 hours to obtain ammonium type borosilicate.

In this ammonium borosilicate, $SiO_2/B_2O_3$ (molar ratio) was 170/1. On calcining this ammonium type borosilicate in the air at 550° C. for 4 hours, H type crystalline borosilicate was obtained.

REFERENCE EXAMPLE 6

Preparation of Crystalline Ferrosilicate

In 250 ml of water was dissolved 8.24 g of iron (III) nitrate, and 17.6 g of concentrated sulfuric acid and 26.3 g of tetra-n-propylammonium bromide were added thereto to form Solution A. Separately, 211.0 g of water glass (trade name "J Sodium Silicate No. 3", produced by Nippon Kagaku Kogyo Co., Ltd.) was dissolved in 250 ml of water to form Solution B. Separately, 79.0 g of sodium chloride was dissolved in 122 ml of water to form Solution C.

Using Solutions A, B and C as prepared above, 48.2 g of sodium type ferrosilicate was obtained in the same manner as in Reference Example 2. Also in the same manner as in Reference Example 2, ammonium type ferrosilicate wherein the $SiO_2/Fe_2O_3$ (molar ratio) was 100/1 was obtained, and then H type crystalline ferrosilicate was obtained.

EXAMPLE 1

A fixed bed flow type reaction tube was charged with 1.06 g of the crystalline aluminosilicate (I) as obtained in Reference Example 1. While maintaining the temperature at 350° C., a mixture of monoethanolamine and water (monoethanolamine/water (weight ratio)=½) was introduced in the reaction tube in a hydrogen stream (204 ml/min, calculated at 20° C.) under conditions of reaction pressure 4 kg/cm² (absolute pressure) and GHSV 10,200 hr⁻¹. Triethylenediamines were obtained in a yield of 21.0% and 64.8% of the monoethanolamine as the starting material was recovered as the unreacted compound.

EXAMPLES 2 TO 4

The procedure of Example 1 was repeated with the exception that the reaction pressure was changed to 7 kg/cm² (absolute pressure) (Example 2), 11 kg/cm² (absolute pressure) (Example 3), or 50 kg/cm² (absolute pressure) (Example 4).

The results are shown in Table 1.

COMPARATIVE EXAMPLE 1

The procedure of Example 1 was repeated with the exception that the reaction pressure was changed to 1 kg/cm² (absolute pressure).

The results are shown in Table 1.

EXAMPLES 5 TO 7

The procedure of Example 1 was repeated with the exception that the amount of the crystalline aluminosilicate (I) used was changed to 2.0 g (Example 5), 4.0 g (Example 6) or 7.7 g (Example 7), or while maintaining the reaction pressure at 7 kg/cm² (absolute pressure), GHSV was changed to 5,400 hr⁻¹ (Example 5), 2,700 hr⁻¹ (Example 6) or 1,400 hr⁻¹ (Example 7).

The results are shown in Table 1.

EXAMPLE 8

The procedure of Example 6 was repeated with the exception that the reaction temperature was changed to 300° C.

The results are shown in Table 1.

COMPARATIVE EXAMPLE 2

The procedure of Example 8 was repeated with the exception that the reaction pressure was changed to 1 kg/cm² (absolute pressure).

The results are shown in Table 1.

EXAMPLES 9 TO 10

The procedure of Example 6 was repeated with the exception that the crystalline aluminosilicate (I) was replaced by the crystalline aluminosilicate (II) (Example 9), or by the crystalline aluminosilicate (III) (Example 10).

The results are shown in Table 1.

EXAMPLES 11 TO 12

The procedure of Example 6 was repeated with the exception that the crystalline aluminosilicate (I) was replaced by crystalline gallosilicate (Example 11), or crystalline borosilicate (Example 12).

The results are shown in Table 1.

EXAMPLES 13 TO 18

The procedure of Example 6 was repeated with the exception that the monoethanolamine was replaced by diethanolamine (Example 13), piperazine (Example 14), morpholine (Example 15), ethylenediamine (Example 16), N-hydroxyethylpiperazine (Example 12) or N-aminoethylpiperazine (Example 18).

The results are shown in Table 1.

TABLE 1

| Run No. | Amine Compound | Yield of Tri-ethylene-diamines (%) | Rate of Recovery of Unreacted Starting material (%) |
| --- | --- | --- | --- |
| Example 2 | Monoethanolamine | 31.7 | 40.7 |
| Example 3 | " | 32.7 | 28.1 |
| Example 4 | " | 31.3 | 29.8 |
| Example 5 | " | 68.2 | 14.0 |
| Example 6 | " | 71.6 | 0.5 |
| Example 7 | " | 53.4 | 0 |
| Example 8 | " | 24.0 | 41.0 |
| Example 9 | " | 63.0 | 0.9 |
| Example 10 | " | 38.4 | 23.8 |
| Example 11 | " | 54.9 | 6.0 |
| Example 12 | " | 41.1 | 28.2 |
| Example 13 | Diethanolamine | 28.4 | 8.2 |
| Example 14 | Piperazine | 50.6 | 40.6 |
| Example 15 | Morpholine | 30.2 | 10.7 |
| Example 16 | Ethylenediamine | 40.1 | 23.0 |
| Example 17 | N-Hydroxyethyl-piperazine | 65.3 | 26.9 |
| Example 18 | N-Aminoethyl-piperazine | 50.7 | 38.1 |
| Comparative Example 1 | Monoethanolamine | 9.3 | 85.7 |
| Comparative Example 2 | " | 8.8 | 73.2 |

What is claimed is:

1. A process for preparing triethylenediamines which comprises contacting an amine compound selected from the groups consisting of monoethanolamine, piperazine, ethylenediamine and N-aminoethylpiperazine with a catalyst comprising crystalline metallosilicate having a silica ($SiO_2$)/metal oxide ($M_2O_3$) molar ratio of 12/1 or more under a pressure of not less than 4 kg/cm$^2$ (absolute pressure), said M is at least one metal selected from the group consisting of gallium and boron.

2. The process as claimed in claim 1 wherein the silica ($SiO_2$)/metal oxide ($M_2O_3$) molar ratio is 40/1 to 3000/1.

3. The process as claimed in claim 2 carried out under a pressure of from 6 to 150 kg/cm$^2$ (absolute pressure).

4. The process as claimed in claim 1 wherein M is gallium.

5. The process as claimed in claim 1 wherein the crystalline metallosilicate has a large pore made of ten-membered ring of oxygen.

6. The process as claimed in claim 1 wherein M is boron.

* * * * *